US012305507B2

(12) United States Patent
Albassam et al.

(10) Patent No.: US 12,305,507 B2
(45) Date of Patent: May 20, 2025

(54) MEASURING DRILLING FLUID HYDROGEN SULFIDE WITH SMART POLYMERS

(71) Applicant: Saudi Arabian Oil Company, Dhahran (SA)

(72) Inventors: Mohammed Albassam, Alkhobar (SA); Arturo Magana Mora, Dhahran (SA); Chinthaka Pasan Gooneratne, Dhahran (SA); Mohammad Aljubran, Sayhat (SA); Peter Boul, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 419 days.

(21) Appl. No.: 17/960,350

(22) Filed: Oct. 5, 2022

(65) Prior Publication Data
US 2024/0117737 A1 Apr. 11, 2024

(51) Int. Cl.
*E21B 49/08* (2006.01)
*C09K 8/24* (2006.01)
(Continued)

(52) U.S. Cl.
CPC ............ *E21B 49/0875* (2020.05); *C09K 8/24* (2013.01); *G01N 33/2841* (2013.01); *E21B 21/068* (2013.01)

(58) Field of Classification Search
CPC .............. E21B 21/068; E21B 49/0875; G01N 33/2841; C09K 8/24
See application file for complete search history.

(56) References Cited

U.S. PATENT DOCUMENTS 10,905,636 B2 * 2/2021 Musa .................. A61K 8/8152
11,939,827 B1 3/2024 Albassam et al.
(Continued)

OTHER PUBLICATIONS

Bhattacharya et al., "Mechanical-Bending-Induced Fluorescence Enhancement in Plastically Flexible Crystals of a GFP Chromophore Analogue," Angewandte Chemie, Jul. 2020, 132(45):20050-20055, 6 pages.
(Continued)

*Primary Examiner* — Lisa M Caputo
*Assistant Examiner* — Nyla Gavia
(74) *Attorney, Agent, or Firm* — Fish & Richardson P.C.

(57) ABSTRACT

Systems and methods include techniques for using smart polymers. Units of smart polymers with hydrogen sulfide (H2S) sensitivity are inserted by a monitoring system into drilling fluid pumped into a well. The smart polymers are configured to be triggered by increasing H2S concentrations. An insertion timestamp associated with each unit is stored. Each insertion timestamp indicates a time that each unit was inserted. Continuous images and observed characteristics of returning mud exiting through an annulus of the well and containing the units of smart polymer are captured by a camera positioned at a sensing location and linked to the monitoring system. An estimate of H2S levels at a drill bit of the drilling operation is determined using continuous images, observed characteristics, and insertion timestamps, and based at least in part on executing image processing algorithms, machine-learning models, and deep-learning models. Changes to drilling parameters are suggested.

20 Claims, 8 Drawing Sheets

(51) Int. Cl.
*E21B 21/06* (2006.01)
*G01N 33/28* (2006.01)

(56) References Cited

U.S. PATENT DOCUMENTS

| | | | |
|---|---|---|---|
| 2009/0128818 A1* | 5/2009 | Goodwin | G01N 33/2823 356/326 |
| 2010/0258304 A1* | 10/2010 | Hegeman | E21B 47/10 175/50 |
| 2012/0031303 A1* | 2/2012 | Constantz | C04B 14/26 106/640 |
| 2016/0272869 A1* | 9/2016 | Singh | C09K 8/725 |
| 2019/0375978 A1* | 12/2019 | Shojaei | E21B 21/002 |
| 2019/0382519 A1* | 12/2019 | Musa | A61K 8/06 |
| 2020/0190959 A1* | 6/2020 | Gooneratne | G01N 21/8851 |
| 2024/0110476 A1 | 4/2024 | Albassam et al. | |
| 2024/0117738 A1 | 4/2024 | Albassam et al. | |
| 2024/0118213 A1 | 4/2024 | Albassam et al. | |

OTHER PUBLICATIONS

Guo et al., "Fluorescence Chemosensors for Hydrogen Sulfide Detection in Biological Systems," Analyst, Mar. 2015, 140(6):1772-1786, 18 pages.

Gustafson et al., "Design of Irreversible Optical Nanothermometers for Thermal Ablations," Chemical Communications, Jan. 2013, 49(7):680-682, 3 pages.

Han et al., "Fluorescent Indicators for Intracellular pH," Chem. Rev., May 2010, 110(5):2709-2728, 20 pages.

Herrmann, "Dynamic Combinatorial/Covalent Chemistry: A Tool to Read, Generate and Modulate the Bioactivity of Compounds and Compound Mixtures," Chemical Society Reviews, Mar. 2014, 43(6):1899-1933, 36 pages.

Li et al., "Dually emitting carbon docts as fluorescent probes for ratiometric fluorescent sensing of pH values, mercury(II), chloride and Cr(VI) via different mechanisms," Microchimica Acta, May 2019, 186(6):341, 10 pages.

Qu et al., "Polyethyleneimine-templated Ag nanoclusters: A new fluorescent and colorimetric platform for sensitive and selective sensing halide ions and high disturbance—tolerant recognitions of iodide and bromide in coexistence with chloride under condition of high ionic strength," Analytical Chemistry, Nov. 2012, 84(23):10373-10379, 7 pages.

Stefani et al., "Thermochromic Fluorophores and Their NIR Laser Induced Transformation," Chemistry of Materials, Dec. 2006, 18(26):6115-6120, 6 pages.

Tollan et al., "Irreversible Thermochromic Behavior in Gold and Silver Nanorod/Polymeric Ionic Liquid Nanocomposite Films," ACS Applied Materials & Interfaces, Feb. 2009, 1(2):348-352, 5 pages.

Yu et al., "Carbon-Dot-Based Ratiometric Fluorescent Sensor for Detecting Hydrogen Sulfide in Aqueous Media and inside Live Cells," Chemical Communications, Jan. 2013, 49(4):403-405, 3 pages.

* cited by examiner

MEASURING DRILLING FLUID HYDROGEN SULFIDE WITH SMART POLYMERS

TECHNICAL FIELD

The present disclosure applies to measuring and estimating conditions while drilling wells, e.g., oil wells.

BACKGROUND

Hydrogen sulfide, more commonly known as H2S (or $H_2S$), is a colorless, flammable, extremely hazardous gas that is often characterized by a "rotten egg" smell when present in small concentrations. H2S is extremely dangerous as it is poisonous, corrosive, and flammable. H2S occurs naturally in crude oil, natural gas, and other organic materials. H2S concentration is typically measured in parts per million (ppm) and the recommended exposure limit (REL) is 10 ppm as a ceiling limit. Monitoring H2S concentration at the surface, such as in oil drilling operations, is essential to ensure that workers do not get exposed to high levels of H2S that may cause short- or long-term consequences. Detection of H2S concentrations should never rely on the sense of smell because loss of smell occurs after exposure to 100 parts per million (ppm) over a time period of 2-15 minutes. In addition, monitoring H2S downhole (as opposed to the surface) provides more data on the formations being drilled as well as making it possible to inform a rig crew of the maximum H2S measurements downhole. In addition, monitoring H2S downhole provides more data on the formations being drilled as well as informing the rig crew of the maximum H2S measurements downhole. This can allow the rig crew to take extra precautions at the surface.

Hydrogen sulfide is heavier than air and may travel along the ground. The gas can tend to accumulate in low-lying and enclosed, poorly-ventilated areas, such as basements, manholes, sewer lines, underground telephone vaults, and manure pits. Hydrogen sulfide is both an irritant and a chemical asphyxiate with effects on both oxygen utilization and the central nervous system. Hydrogen sulfide's health effects can vary depending on the level and duration of exposure. Repeated exposure can result in health effects occurring at levels that may have been previously tolerated without any health effect.

Low H2S concentrations irritate the eyes, nose, throat, and respiratory system (e.g., causing burning/tearing of eyes, cough, and shortness of breath). People with asthma may experience breathing difficulties. The effects can be delayed for several hours, or sometimes several days, when working in low-level concentrations. Repeated or prolonged exposures may cause eye inflammation, headache, fatigue, irritability, insomnia, digestive disturbances, and weight loss.

Moderate concentrations of hydrogen sulfide can cause more severe eye and respiratory irritation (e.g., coughing, difficulty breathing, and accumulation of fluid in the lungs), headache, dizziness, nausea, vomiting, staggering, and excitability. High concentrations can cause shock, convulsions, inability to breathe, extremely rapid unconsciousness, coma, and death. Effects can occur within a few breaths, and possibly a single breath.

SUMMARY

The present disclosure describes techniques that can be used to estimate hydrogen sulfide (H2S or $H_2S$) concentrations at a drill bit during a drilling operation through the use of smart polymers introduced into drilling fluid and photographed in returning drilling mud after exposure to downhole conditions. The techniques can include the use of H2S-responsive polymers to measure the H2S in the oil and gas industry.

In some implementations, a computer-implemented method includes the following. Units of smart polymers with hydrogen sulfide (H2S) sensitivity are inserted by a monitoring system into drilling fluid pumped into a well during a drilling operation. The smart polymers are configured to be triggered by increasing H2S concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of H2S levels at a drill bit of the drilling operation is determined by the monitoring system using the continuous images and the observed characteristics and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the H2S levels.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. The techniques of the present disclosure can provide a robust, efficient way to measure downhole H2S concentrations. Currently, there are no available methods to measure downhole H2S levels while drilling. The techniques of the present disclosure can enable the capability of having multiple H2S downhole measurements, as well as evaluating different formations that are being drilled. Moreover, the technologies incorporated in the techniques of the present disclosure can take advantage of emerging technologies aligned with the fourth industrial revolution (4IR), such as automation, Internet of Things (IoT), artificial intelligence (AI) machine learning, and data analytics. The techniques of the present disclosure can include using a camera at the shale shaker and smart polymers to measure downhole H2S concentration. This can help to understand the reservoir and provide information at the surface which can help regarding health and safety issues.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Figure 1:
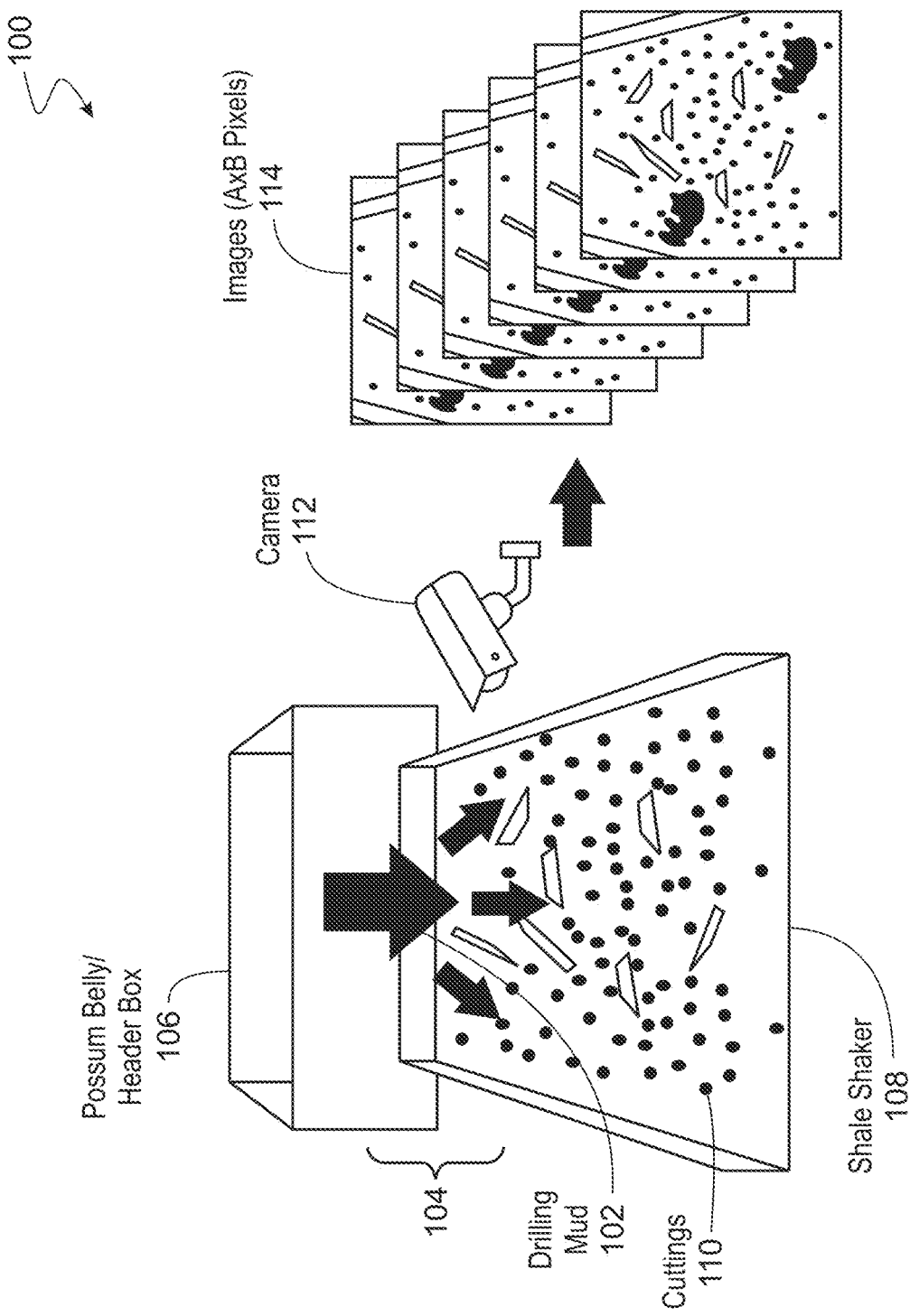
FIG. 1 is a plan view of an example of a shale shaker configuration, according to some implementations of the present disclosure.

The following detailed description describes techniques used to estimate hydrogen sulfide (H2S or $H_2S$) concentrations at a drill bit during a drilling operation through the use of smart polymers. The smart polymers can be introduced into drilling fluid and photographed in returning drilling mud after exposure to downhole conditions. Various modifications, alterations, and permutations of the disclosed implementations can be made and will be readily apparent to those of ordinary skill in the art, and the general principles defined may be applied to other implementations and applications, without departing from the scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

The present disclosure describes techniques that use smart fluids/polymers and a camera recording drilling mud returns at a shale shaker to predict H2S concentrations at the surface and downhole. Smart polymers include stimuli-responsive polymers that change properties according to the environment in which they are placed. Different stimuli include pressure, temperature, pH, and ionic strength, for example. Changes in properties include shape, chemical properties, and color. The present disclosure focuses on H2S as a trigger to change the color/intensity of smart polymers/fluids that are detected by a camera at the shale shaker. For example, the presence of H2S downhole can be used as a trigger to change the color/intensity of smart polymers/fluids that can be automatically detected by computational models to analyze frames obtained by the camera recording.

The present disclosure describes a system using smart polymers that react to H2S stimuli and an Internet of things (IoT) platform to be used at a drilling rig. The system includes: 1) smart, waterproof, high-resolution, wireless cameras (or any other image or vision sensor, including infrared, gamma ray, CT scan, x-ray, capable of image/video capture at shale shakers; 2) edge/fog computing hardware; and 3) software for image/video processing to transform discrete images to numerical values representing H2S concentrations in real-time.

The continuous measurement of the H2S concentrations is an essential task due to health and safety risks. Consequently, the present disclosure describes techniques that use smart fluids/polymers and a camera at the shale shaker to measure H2S levels downhole and at the surface. Smart polymers are stimuli-responsive polymers that change properties according to the environment they are placed in. Different stimuli include temperature, pH, or ionic strength, among others. Changes in properties can include changing shape, chemical properties, emitting light, or color. The present disclosure describes the use of H2S as a trigger to change the color/intensity of smart polymers/fluids that can be automatically detected by computational models to analyze the frames obtained by the camera recording the shale shaker.

There are two types of stimuli-responsive polymers: reversible and irreversible. Reversible polymers return to their natural state once a trigger has been eliminated from the environment. On the other hand, irreversible polymers do not return back to their initial state when the trigger is removed. The present disclosure focuses on both reversible and irreversible polymers for measuring the H2S concentrations. Irreversible polymers make it possible to measure maximum H2S concentrations downhole, which may be higher than what reaches the surface (as dilution has yet to occur.) This is extremely useful because H2S surface measurements do not necessarily reflect the concentration downhole at specific formations. However, as an H2S source mixes with mud and travels to the surface, the H2S gets diluted due to lower H2S concentration environments (e.g., drilling fluid with zero or low H2S concentrations). Reversible polymers reaching the surface are adaptive to the H2S levels at that current depth. This adaptability allows the camera at the shale shaker to detect H2S concentration levels at the surface, which is important to ensure a safe drilling environment and to eliminate health and safety risks.

The present disclosure addresses current limitations with downhole H2S measurements, including a primary limitation in which there are no available tools that can measure downhole H2S content while drilling. In current conventional systems, H2S concentrations provided to drilling crews are measured using a process of collecting fluids samples from the reservoir in a pressurized chamber. The samples are then sent to a lab to perform a fluid composition analysis (FCA) where H2S and other properties are measured. This process can take significant time to complete. However, using techniques of the present disclosure, the use of smart polymers to measure H2S in downhole conditions provides a fast and robust way to obtain critical data regarding drilled formation. Such a process can be performed automatically, multiple times each day.

Using techniques of the present disclosure, smart polymers (e.g., in the shape of pills) can be designed to be pumped with the drilling fluid. For example, the pills can be pumped with the drilling fluid at different intervals (e.g., every 1/3/5 minutes) or can be pumped every one stand (e.g., every 90 feet). The H2S polymers can be designed to be triggered by H2S concentrations. The H2S-responsive polymers change properties as a function of the H2S levels in the environment applied. As the pills exit the well through the annulus, a camera at the shale shaker can capture continuous images of the returning mud and uses image processing algorithms as well as machine-learning (ML)/deep-learning (DL) models to predict/estimate H2S levels.

FIG. 1 is a plan view of an example of a shale shaker configuration 100, according to some implementations of the present disclosure. Drilling mud flow 102 direction is represented by arrows 104. The mud enters a solids control process from a possum belly/header box 106. In this example, gravity feeds the mud into the vibrating basket of a shale shaker 108, loaded with course and fine mesh screens designed to sort the solids (e.g., cuttings 110) from the liquid phase. The mud moves from top to bottom, as shown in FIG. 1, through a motion caused by shaker basket vibration. As the drilling mud travels, the vibrational impact with the screen causes liquid/solid separation and/or drying. Upon discharge at the bottom of the shale shaker 108, the solids are discarded (as shown) while the liquid (and fine solids, depending on screen size) pass into the sump tank for further treatment and ultimate recycling for re-pumping downhole. A camera 112 is used to capture images 114, e.g., of dimension size A×B. The images 114 are processed by image processing algorithms and machine learning to convert analog data (e.g., intensity, color, and light) to digitized numerical H2S data. Vision sensing can occur at multiple locations using multiple cameras, for example, at solids discharge from one or more of the shale shaker, centrifuges, de-sanders, de-silters, and locations using other solids control technologies. However, the present disclosure focuses on the shale shaker, with surface screening of solids in a load and discharge configuration as shown in FIG. 1.

The camera at the shale shaker along with H2S sensitive polymers offer a new method to measure H2S. The novelty of the techniques of the present disclosure is not in the polymer formulation as these are well established in the literature and science. The novelty comes in using H2S-responsive polymers to measure H2S levels at the surface and downhole, e.g., in the oil and gas industry. In addition, the present disclosure utilizes ML/DL models that are capable of converting digital numerical H2S values using images data. Consequently, the methods described in the present disclosure have the following applications: measuring H2S concentration at the surface, and measuring the maximum downhole H2S concentration.

Figure 2:
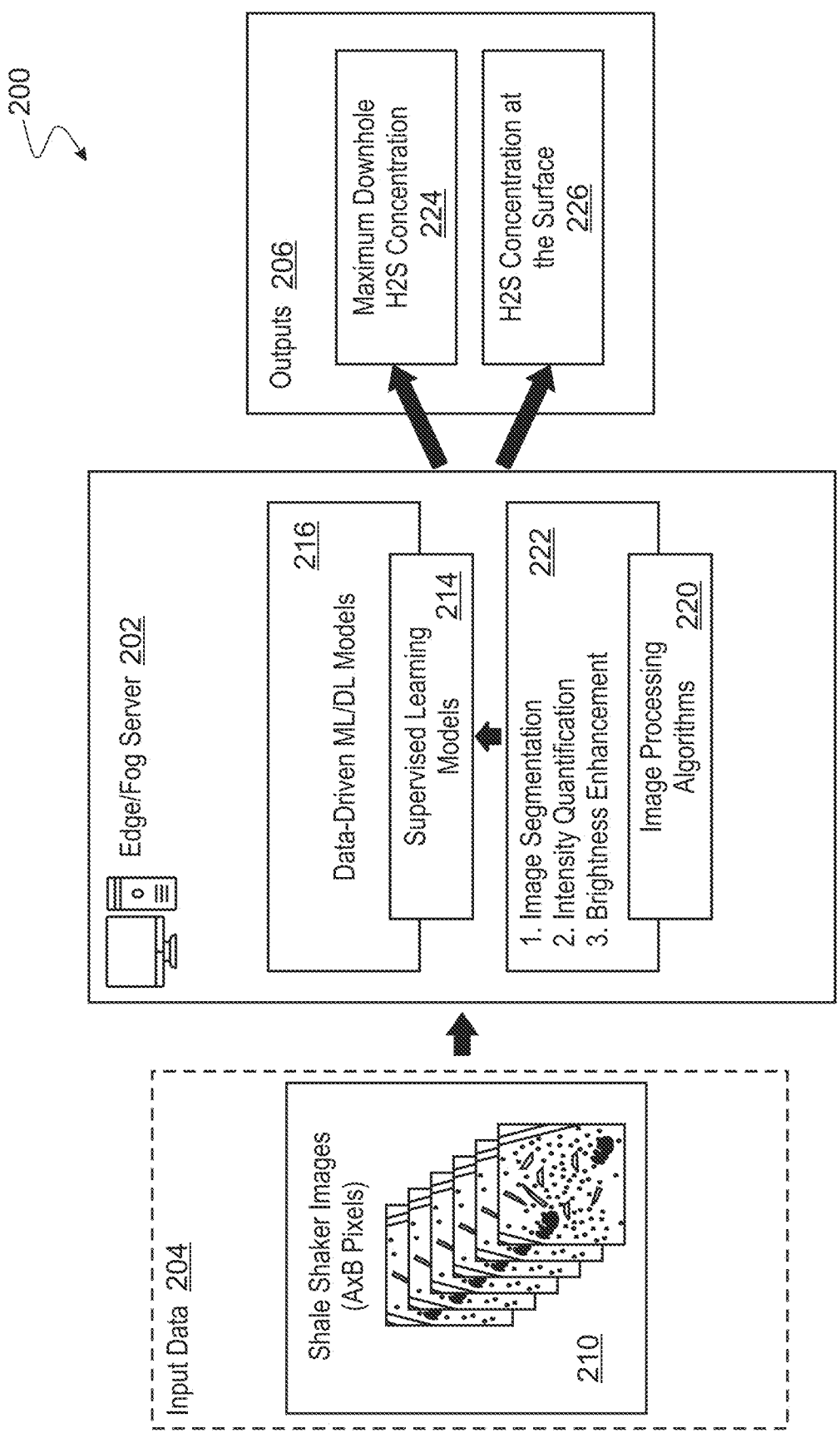
FIG. 2 is a drawing showing an example of inputs and outputs of a system for measuring hydrogen sulfide (H2S), according to some implementations of the present disclosure.

FIG. 2 is a drawing showing an example of inputs and outputs of a system 200 for measuring H2S, according to some implementations of the present disclosure. The system 200 includes an edge/fog server 202 that processes input data 204 for the system 200 and generates outputs 206.

The input data 204 can include image data (e.g., shale shaker images 210). The edge/fog server 202 can use various models, including supervised learning models 214, which can serve as inputs to data-driven ML/DL models 216. The supervised learning models 214 can use as input outputs of image processing algorithms 220 that can perform functions 222 including image segmentations, intensity quantification, and brightness enhancement. The outputs 206 include a maximum downhole H2S concentration 224 and an H2S concentration at the surface 226.

Image data from the camera/vision sensors are expected to be primarily processed in continuous recording to capture the trends of the flow over time. Frames from the camera can be processed by the image processing algorithms 220 and ML/DL models 216 deployed in the edge/fog server 202. The methods described in the present disclosure can use a set of image processing techniques to detect the polymer intensity/color in the frame as well as to enhance the contrast and brightness of the frames. The image processing techniques can include pixilation, image segmentation, intensity quantification, and supervised learning models (including ML and DL). Algorithms can be used to convert the images to arrays that can be later translated to numerical values describing the H2S concentrations in ppm.

To develop and train an ML model, smart polymers pills can be exposed to different H2S concentrations in the lab. Specific H2S levels can be applied to the smart polymers pills, and images of the resulting polymers can be acquired. These images, along with the actual applied H2S concentrations, can then be used to train ML/DL models. The laboratory data can then be used in the learning phase of the model, as data points represent the targets/labels, as described with reference to FIG. 3. After the model is derived, an objective of the model is the ability to predict H2S levels based on returning drilling fluid H2S concentration using the images captured and processed during real-time drilling operations.

The numerical representation of the intensities of the polymers mixed with the fluid observed at the shale shakers can be directly used to estimate H2S levels. For instance, a simple logistic regression model may be used as follows:

$$H2S \text{ (ppm)} = \beta \times \max(\text{pixel intensity}), \quad (1)$$

where $\beta$ refers to the coefficient learned by the regression model and max(pixel intensity) to the pixel with the highest intensity values in a frame, respectively. H2S refers to the H2S values as measured in the laboratory, e.g., measured in ppm. A linear regression, e.g., using a supervised learning model, can learn this relationship by observing multiple samples S with their respective target labels (H2S).

However, relying on the value of a single pixel intensity may not provide enough accuracy. Consequently, supervised learning DL models, such as convolutional neural networks (CNN), auto encoder neural networks (AE-NN), among others, can be derived from the frames to classify the observed polymer intensity/color in the images. These models can consider the set of polymer intensities in the entire frame. Additional image processing algorithms can be used to crop the image, increase the brightness, or optionally select only a region of the image (image segmentation). The processed images can then be fed into DL models to automatically extract abstract features from the frames that can be linked to the H2S as a target. In supervised learning, each frame containing the set of intensities observed from the smart polymer can be assigned a label (e.g., H2S in ppm) to train the ML model, as shown in FIG. 3.

To label the data (frames with their respective label), the smart polymers pills can be exposed to different H2S concentrations in the lab. Certain H2S levels can be applied, and images of the resulting polymers can be acquired. These images along with the actual applied H2S concentrations can then be used to train the machine model. Notably, the laboratory data can be required for the learning phase of the model, as these data represent the targets/labels. After the model is derived, the objective of the model is to predict these values using the images.

Figure 3:
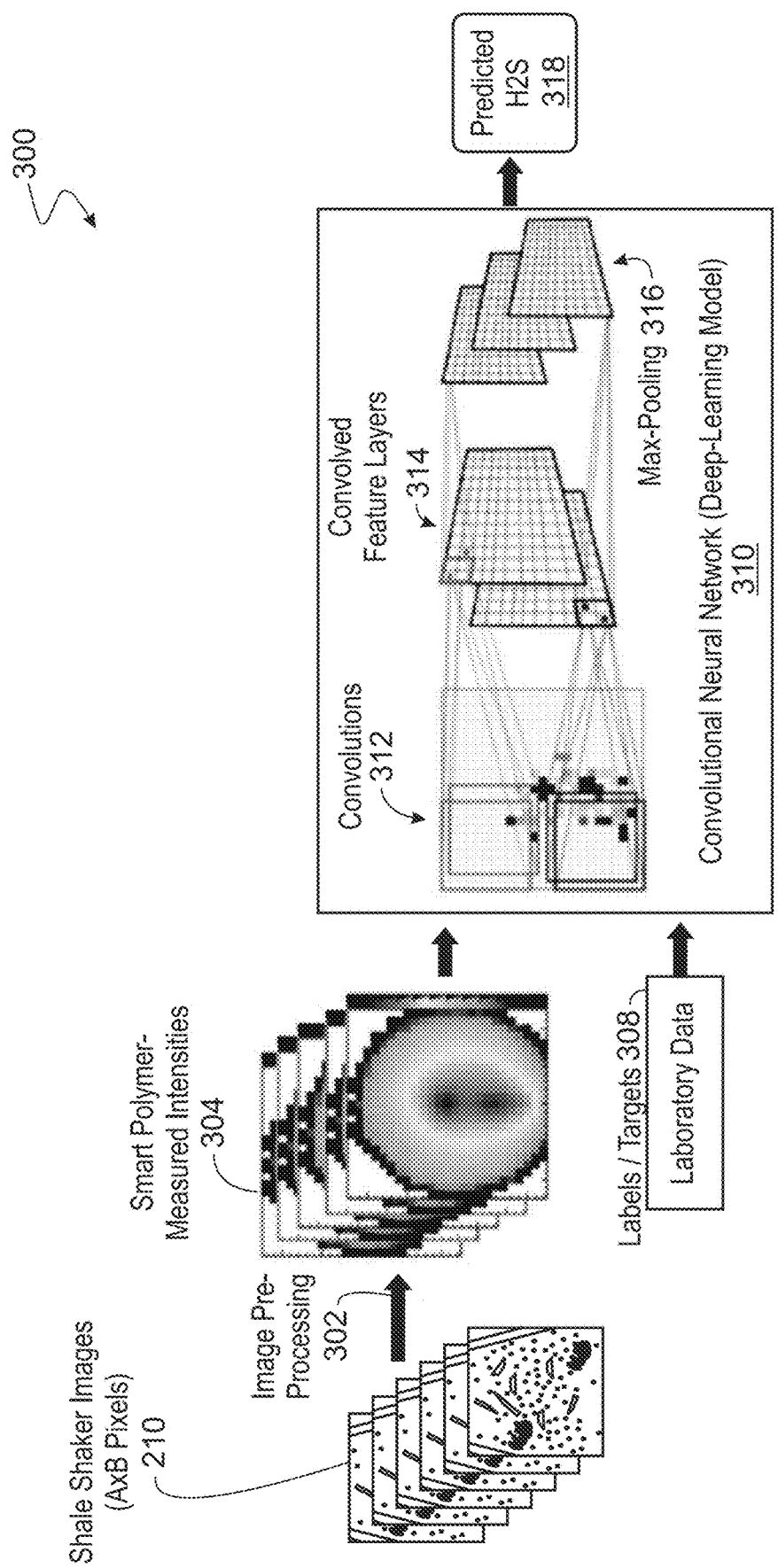
FIG. 3 is a diagram showing an example of a supervised learning method to predict/estimate the H2S concentrations, according to some implementations of the present disclosure.

FIG. 3 is a diagram showing an example of a supervised learning method 300 to predict/estimate the H2S concentrations, according to some implementations of the present disclosure. The supervised learning method 300 can be used as initial input for the shale shaker images 210. Image pre-processing 302 performed on the shale shaker images 210 can create smart polymer measured intensities 304. Labels/targets 308, along with the smart polymer measured intensities 304, can serve as inputs to a Convolutional Neural Network (CNN) (e.g., deep learning model) 310. Convolutions 312 can be used to create convolved feature layers 314 from which max-pooling 316 is performed. Output of the CNN 310 is a predicted H2S concentrations 318.

Conceptual Design

The chemical concept of H2S sensing in the present disclosure has at its core hydrogen sulfide-induced molecular fragmentation. In this procedure, the $H_2S$ reacts with the dye leading to a fragmentation which changes its fluorescence emission spectrum. The fragmentation occurs as a function of concentration of the H2S. The emission spectrum of the dye after exposure to a given quantity of $H_2S$ can then be correlated to the concentration of $H_2S$ with knowledge of the exposure time and temperature.

Figure 4:
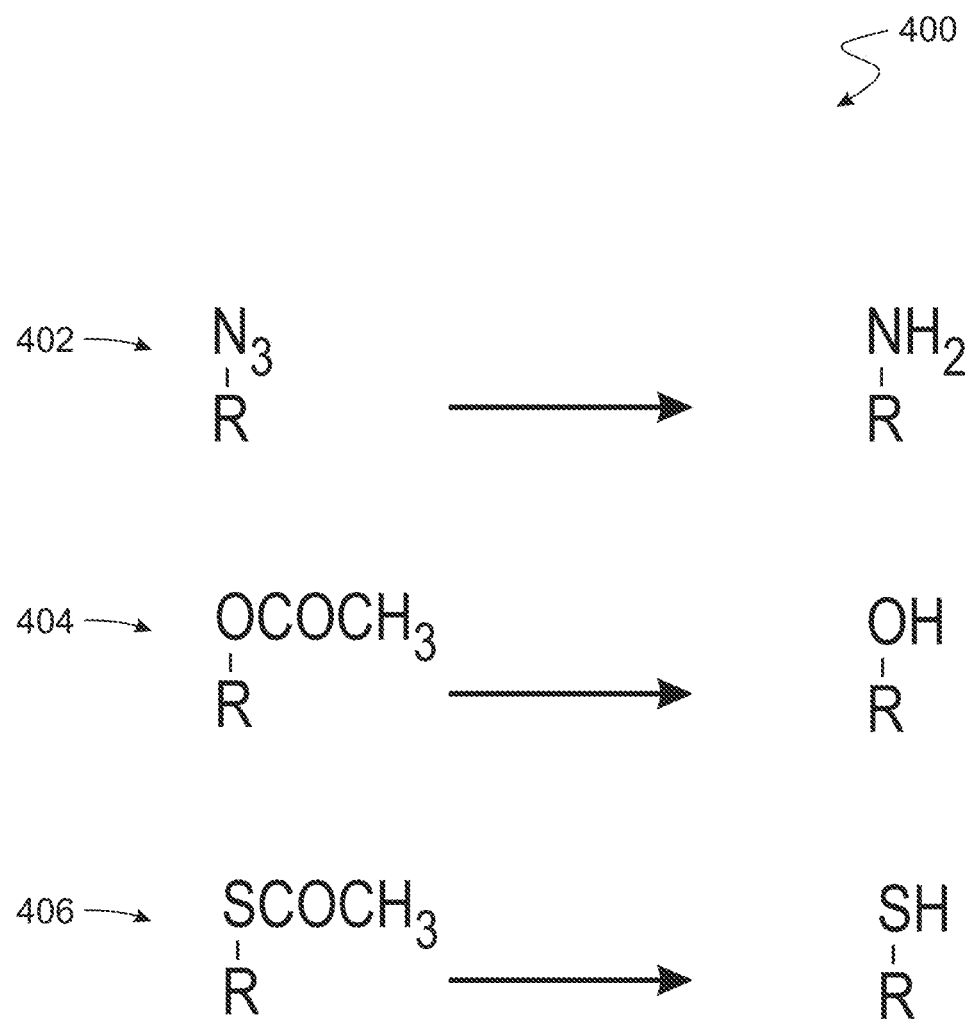
FIG. 4 is a diagram showing an example of a schematic for the fragmentation through three fragmentation reactions regarding H2S sensitivity, according to some implementations of the present disclosure.

FIG. 4 is a diagram showing an example of a schematic 400 for the fragmentation through three fragmentation reactions regarding H2S sensitivity, according to some implementations of the present disclosure. The reactions include a reaction 402 of aryl azide to aryl amine; a reaction 404 of phenyl ester (e.g., phenyl acetate) to phenol; and a reaction 406 of aryl thioester to aryl thiol. The R groups in these reactions are an aromatic, pi-conjugated ring system. In order to have a fluorescence signal within the detectable limits of the CCD camera, the R groups must be pi-conjugated systems with aromaticity. Fragmentation reaction induced by H2S results in products which have different electron withdrawing/electron donating characteristics to their starting materials, resulting in a change in fluorescence emission in the fragmented product as compared with the starting materials.

Specific Examples of $H_2S$ Chemical Sensors

Figure 5:
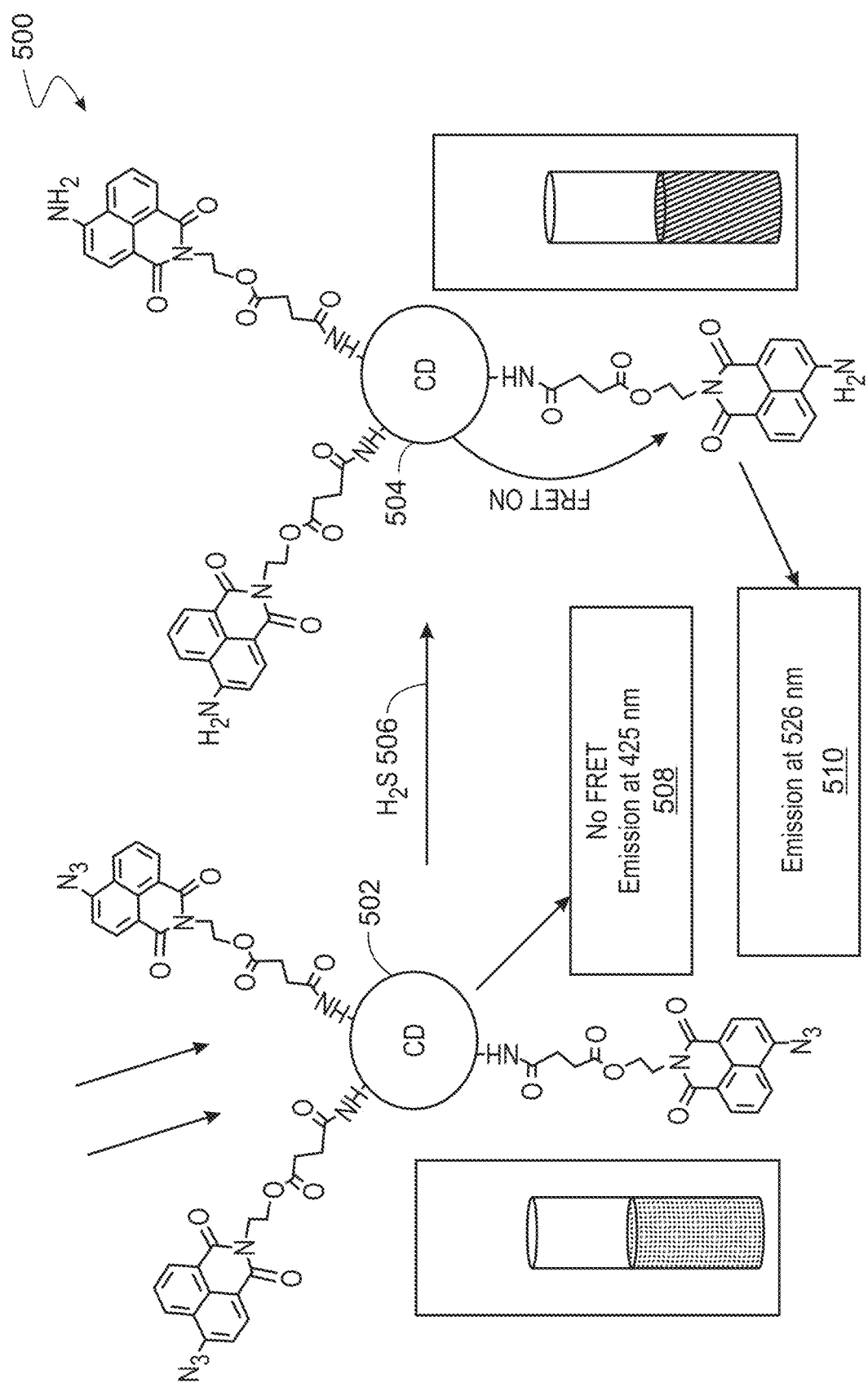
FIG. 5 is a diagram showing an example illustration for the structure of a carbon-dot (CD)-based sensor and its ratiometric detection of H2S, according to some implementations of the present disclosure.

FIG. 5 is a diagram showing an example illustration 500 for the structure of a carbon-dot (CD)-based sensor and its ratiometric detection of H2S, according to some implementations of the present disclosure. A naphthalimide-azide 502 is reduced by H2S 506 to napthalimide-amine 504. This produces a different fluorescence emission due to the activation of a Förster Resonance Energy Transfer (FRET) from the CD to the napthalimide-amine. In this example, there is no FRET emission 508 at 425 nanometers (nm), but there is a FRET emission 510 at 526 nm. FRET is a non-radiative energy transfer process where the excitation energy of an energy donor is transferred to an energy acceptor (in the ground state) through long-range dipole-dipole interactions and/or short-range multipolar interactions. This reduction by H2S is irreversible as each molecule of napthalimide-azide that is reduced by H2S liberates a molecule of N2. The irreversibility of this process is important because drill cuttings with this dye will display the history of exposure of the dye to H2S so long as the sensing mechanism is irreversible. The concentration correspondence of H2S for the dye is shown in FIGS. 6A-6B.

Figure 6A:
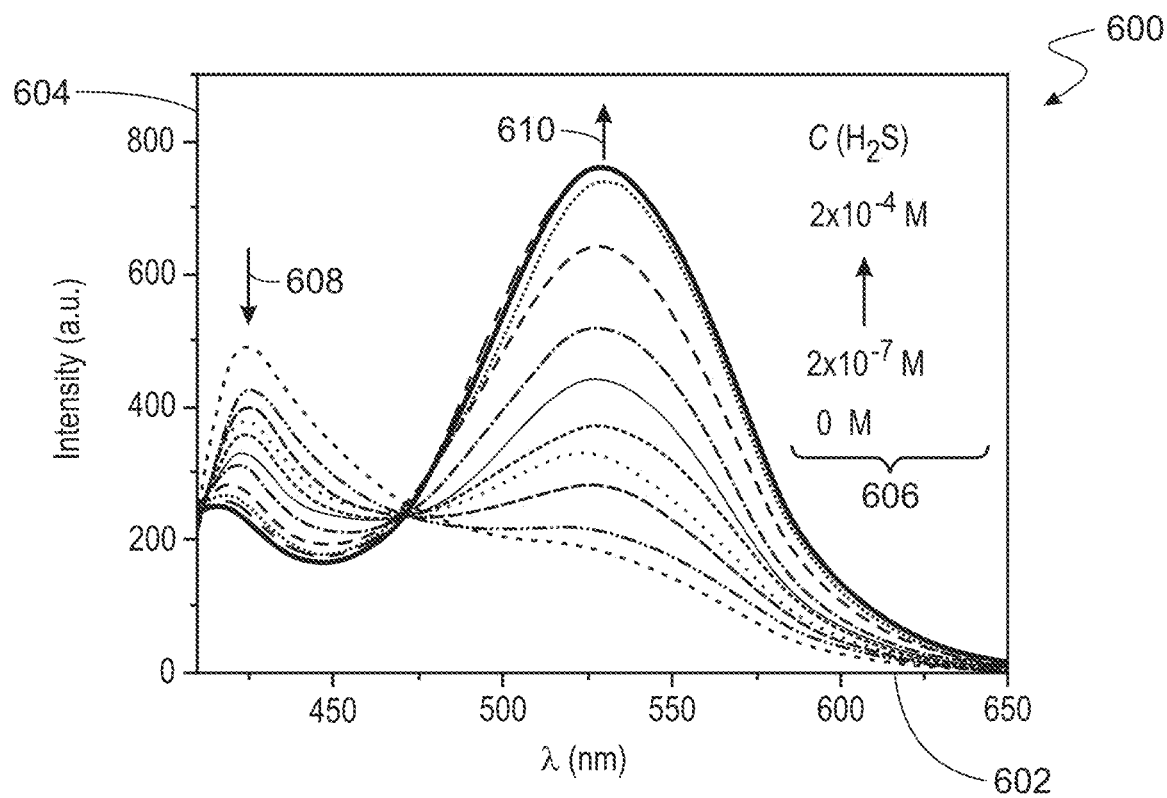
FIG. 6A is a graph showing an example of fluorescence spectra in the presence of different amounts of H2S, according to some implementations of the present disclosure.

FIG. 6A is a graph showing an example of fluorescence spectra 600 in the presence of different amounts of H2S, according to some implementations of the present disclosure. The fluorescence spectra 600 is associated with the CD-based sensor (e.g., at a concentration of 0.45 milligrams/milliliter (mg/mL)). The fluorescence spectra 600 are plotted relative to distance axis 602 (e.g., lambda λ in nm) and intensity axis 604 in arbitrary units (a.u.).

Figure 6B:
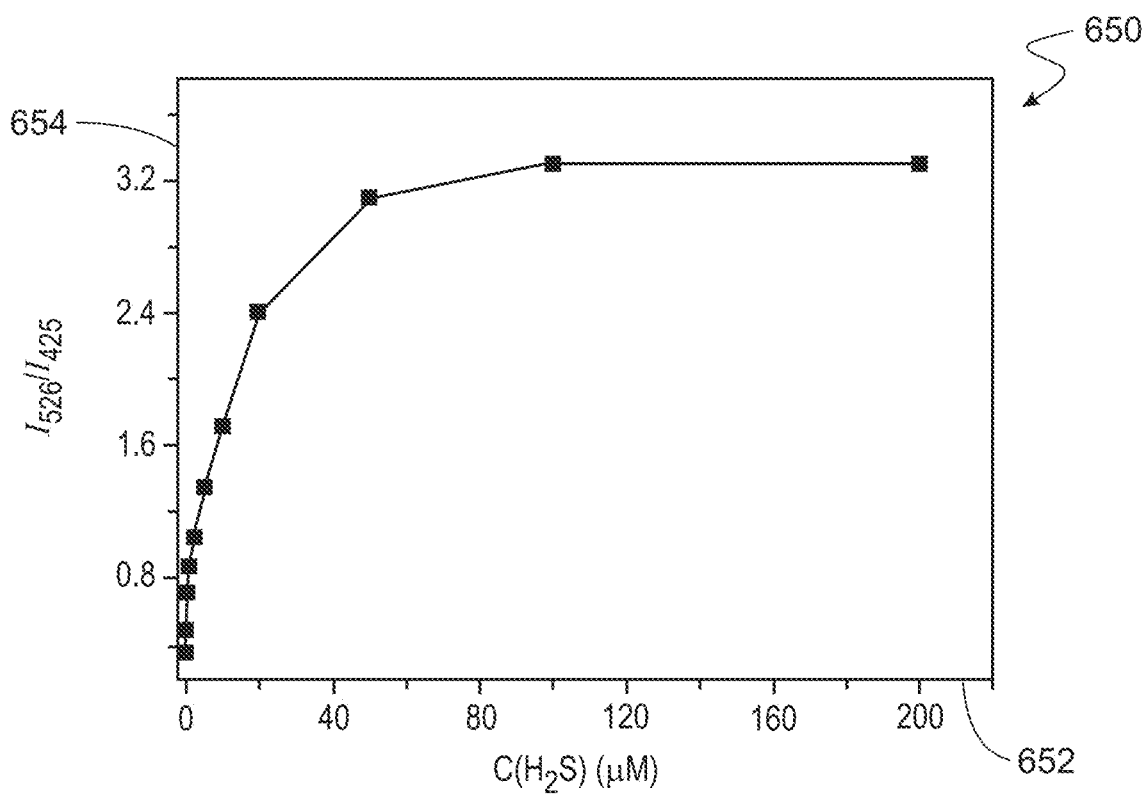
FIG. 6B is a graph showing an example of a fluorescence intensity ratio plot of the CD-based sensor as a function of H2S concentration, according to some implementations of the present disclosure.

FIG. 6B is a graph showing an example of a fluorescence intensity ratio plot 650 of the CD-based sensor as a function of H2S concentration, according to some implementations of the present disclosure. The H2S concentration is in HEPES buffered (e.g., pH 7.4) water-ethanol (3:1, volume/volume (v/v)), (lexc=340 nm)S.

Application to Drilling Fluids

The dyes described above can be added to drilling fluids along with the other mud additives in amounts ranging from $10^{-6}$ percent to 0.1 percent. When the drill cuttings are lifted to surface, some of the dyes from the fluids will remain on the cuttings. These can then be imaged for fluorescence to get an estimation for the exposure of the drilling fluid to the H2S.

Figure 7:
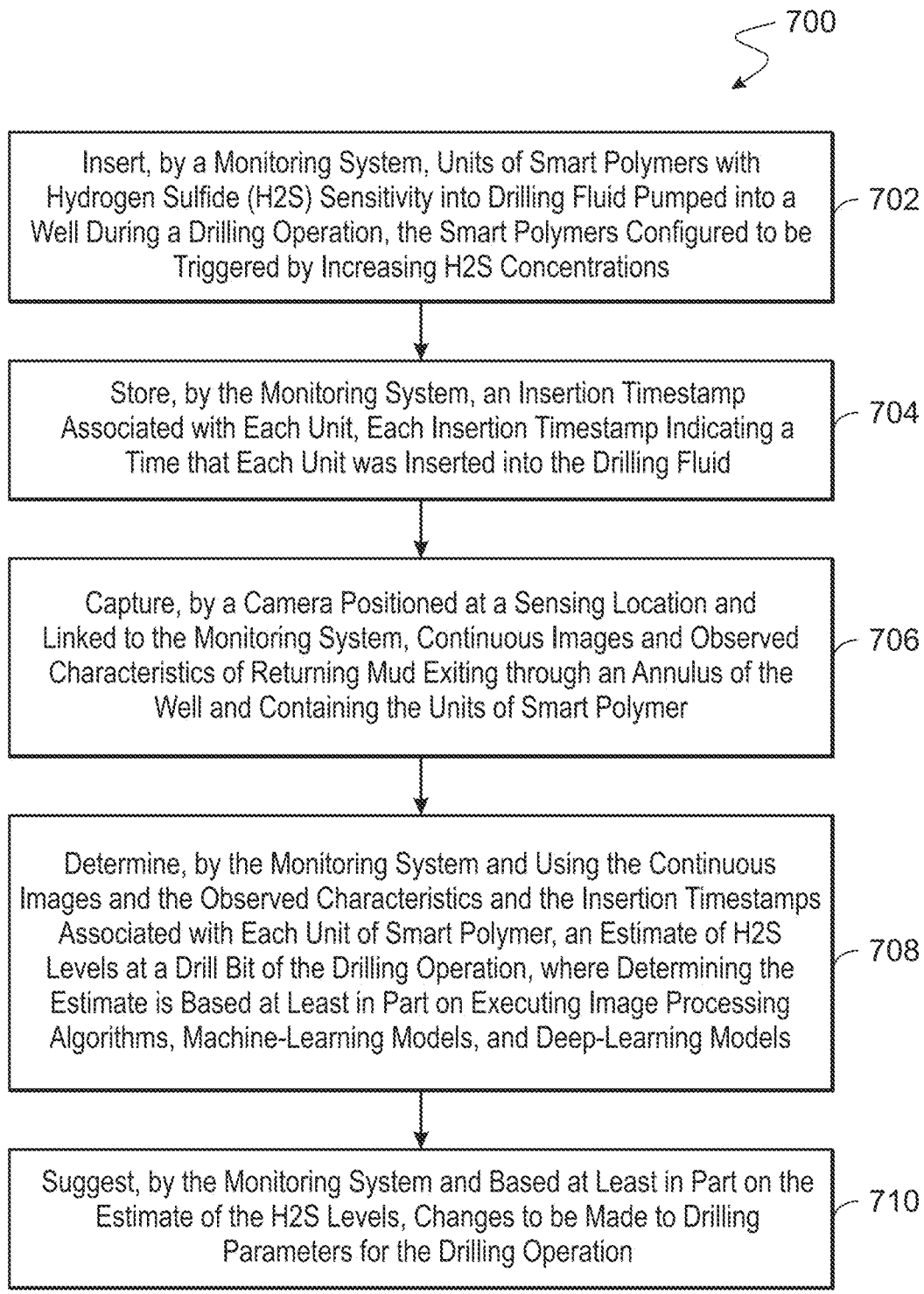
FIG. 7 is a flowchart of an example of a method for estimating H2S levels at a drill bit during a drilling operation through the use of smart polymers introduced into drilling fluid and photographed in returning drilling mud after exposure to downhole conditions, according to some implementations of the present disclosure.

FIG. 7 is a flowchart of an example of a method 700 for estimating H2S levels at a drill bit during a drilling operation through the use of smart polymers introduced into drilling fluid and photographed in returning drilling mud after exposure to downhole conditions, according to some implementations of the present disclosure. For clarity of presentation, the description that follows generally describes method 700 in the context of the other figures in this description. However, it will be understood that method 700 can be performed, for example, by any suitable system, environment, software, and hardware, or a combination of systems, environments, software, and hardware, as appropriate. In some implementations, various steps of method 700 can be run in parallel, in combination, in loops, or in any order.

At 702, units of smart polymers with hydrogen sulfide (H2S) sensitivity are inserted by a monitoring system into drilling fluid pumped into a well during a drilling operation. The smart polymers are configured to be triggered by increasing H2S concentrations. The units of smart polymers can have a pill shape, for example. The units of smart polymers are configured to change properties as a function of changing H2S concentrations exposed to the units of smart polymers by downhole conditions. In some implementations, pumping the units of smart polymers into the drilling fluid can occur at different intervals (e.g., every one, three, or five minutes) or can be pumped every one stand (e.g., every 90 feet). From 702, method 700 proceeds to 704.

At 704, an insertion timestamp associated with each unit is stored by the monitoring system. Each insertion timestamp indicates a time that each unit was inserted into the drilling fluid. From 704, method 700 proceeds to 706.

At 706, continuous images and observed characteristics of returning mud exiting through an annulus of the well and containing the units of smart polymer are captured by a camera positioned at a sensing location and linked to the monitoring system. Capturing the continuous images can include capturing, in the units of smart polymers, evidence of changing H2S levels caused by H2S exposure experienced by the units of smart polymers. The sensing location can be, for example, a shale shaker, a centrifuge, a de-sander, and a de-silter. From 706, method 700 proceeds to 708.

At 708, an estimate of H2S levels at a drill bit of the drilling operation is determined by the monitoring system using the continuous images and the observed characteristics, and the insertion timestamps associated with each unit of smart polymer. Determining the estimate is based at least in part on executing image processing algorithms, machine-learning models, and deep-learning models. Determining the H2S levels can include correlating an arrival timestamp and identifying a time-of-arrival of each unit of smart polymer at the sensing location with a respective hole depth by utilizing a rig sensor for mud flow rate and based on an annular area of the well. From 708, method 700 proceeds to 710.

At 710, changes to be made to drilling parameters for the drilling operation are suggested by the monitoring system based at least in part on the estimate of the H2S levels. For example, changes can be made in drilling parameters that are associated with changes in mud rheology, mud weight, and mud flow rate. After 710, method 700 can stop.

In some implementations, in addition to (or in combination with) any previously-described features, techniques of the present disclosure can include the following. Outputs of the techniques of the present disclosure can be performed before, during, or in combination with wellbore operations, such as to provide inputs to change the settings or parameters of equipment used for drilling. Examples of wellbore operations include forming/drilling a wellbore, hydraulic fracturing, and producing through the wellbore, to name a few. The wellbore operations can be triggered or controlled, for example, by outputs of the methods of the present disclosure. In some implementations, customized user interfaces can present intermediate or final results of the above described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or "app"), or at a central processing facility. The presented information can include suggestions, such as suggested changes in parameters or processing inputs, that the user can select to implement improvements in a production environment, such as in the exploration, production, and/or testing of petrochemical processes or facilities. For example, the suggestions can include parameters that, when selected by the user, can cause a change to, or an improvement in, drilling parameters (including drill bit speed and direction) or overall production of a gas or oil well. The suggestions, when implemented by the user, can improve the speed and accuracy of calculations, streamline processes, improve models, and solve problems related to efficiency, performance, safety, reliability, costs, downtime, and the need for human interaction. In some implementations, the suggestions can be implemented in real-time, such as to provide an immediate or near-immediate change in operations or in a model. The term real-time can correspond, for example, to events that occur within a specified period of time, such as within one minute or within one second. Events can include readings or measurements captured by downhole equipment such as sensors. The readings or measurements can be analyzed at the surface, such as by using applications that can include modeling applications and machine learning. The analysis can be used to generate changes to settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Figure 8:
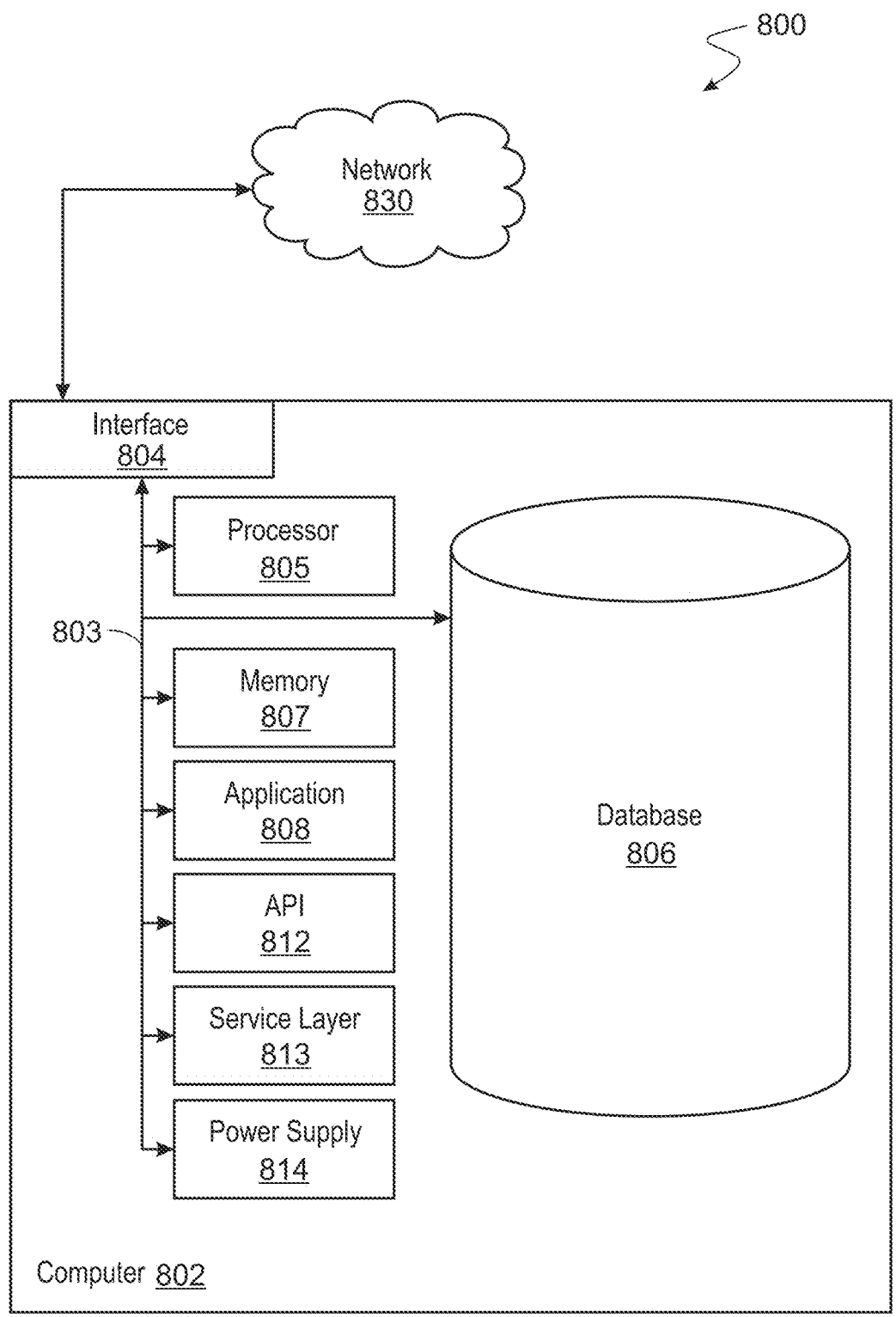
FIG. 8 is a block diagram illustrating an example computer system used to provide computational functionalities associated with described algorithms, methods, functions, processes, flows, and procedures as described in the present disclosure, according to some implementations of the present disclosure.

FIG. 8 is a block diagram of an example computer system 800 used to provide computational functionalities associated with described algorithms, methods, functions, processes, flows, and procedures described in the present disclosure, according to some implementations of the present disclosure. The illustrated computer 802 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 802 can include input devices such as keypads, keyboards, and touch screens that can accept user information. Also, the computer 802 can include output devices that can convey information associated with the operation of the computer 802. The information can include digital data, visual data, audio information, or a combination of information. The information can be presented in a graphical user interface (UI) (or GUI).

The computer 802 can serve in a role as a client, a network component, a server, a database, a persistency, or components of a computer system for performing the subject matter described in the present disclosure. The illustrated computer 802 is communicably coupled with a network 830. In some implementations, one or more components of the computer 802 can be configured to operate within different environments, including cloud-computing-based environments, local environments, global environments, and combinations of environments.

At a top level, the computer 802 is an electronic computing device operable to receive, transmit, process, store, and manage data and information associated with the described subject matter. According to some implementations, the computer 802 can also include, or be communicably coupled with, an application server, an email server, a web server, a caching server, a streaming data server, or a combination of servers.

The computer 802 can receive requests over network 830 from a client application (for example, executing on another computer 802). The computer 802 can respond to the received requests by processing the received requests using software applications. Requests can also be sent to the computer 802 from internal users (for example, from a command console), external (or third) parties, automated applications, entities, individuals, systems, and computers.

Each of the components of the computer 802 can communicate using a system bus 803. In some implementations, any or all of the components of the computer 802, including hardware or software components, can interface with each other or the interface 804 (or a combination of both) over the system bus 803. Interfaces can use an application programming interface (API) 812, a service layer 813, or a combination of the API 812 and service layer 813. The API 812 can include specifications for routines, data structures, and object classes. The API 812 can be either computer-language independent or dependent. The API 812 can refer to a complete interface, a single function, or a set of APIs.

The service layer 813 can provide software services to the computer 802 and other components (whether illustrated or not) that are communicably coupled to the computer 802. The functionality of the computer 802 can be accessible for all service consumers using this service layer. Software services, such as those provided by the service layer 813, can provide reusable, defined functionalities through a defined interface. For example, the interface can be software written in JAVA, C++, or a language providing data in extensible markup language (XML) format. While illustrated as an integrated component of the computer 802, in alternative implementations, the API 812 or the service layer 813 can be stand-alone components in relation to other components of the computer 802 and other components communicably coupled to the computer 802. Moreover, any or all parts of the API 812 or the service layer 813 can be implemented as child or sub-modules of another software module, enterprise application, or hardware module without departing from the scope of the present disclosure.

The computer 802 includes an interface 804. Although illustrated as a single interface 804 in FIG. 8, two or more interfaces 804 can be used according to particular needs, desires, or particular implementations of the computer 802 and the described functionality. The interface 804 can be used by the computer 802 for communicating with other systems that are connected to the network 830 (whether illustrated or not) in a distributed environment. Generally, the interface 804 can include, or be implemented using, logic encoded in software or hardware (or a combination of software and hardware) operable to communicate with the network 830. More specifically, the interface 804 can include software supporting one or more communication protocols associated with communications. As such, the network 830 or the interface's hardware can be operable to communicate physical signals within and outside of the illustrated computer 802.

The computer 802 includes a processor 805. Although illustrated as a single processor 805 in FIG. 8, two or more processors 805 can be used according to particular needs, desires, or particular implementations of the computer 802 and the described functionality. Generally, the processor 805 can execute instructions and can manipulate data to perform the operations of the computer 802, including operations using algorithms, methods, functions, processes, flows, and procedures as described in the present disclosure.

The computer 802 also includes a database 806 that can hold data for the computer 802 and other components connected to the network 830 (whether illustrated or not). For example, database 806 can be an in-memory, conventional, or a database storing data consistent with the present disclosure. In some implementations, database 806 can be a combination of two or more different database types (for example, hybrid in-memory and conventional databases) according to particular needs, desires, or particular implementations of the computer 802 and the described functionality. Although illustrated as a single database 806 in FIG. 8, two or more databases (of the same, different, or combination of types) can be used according to particular needs, desires, or particular implementations of the computer 802 and the described functionality. While database 806 is illustrated as an internal component of the computer 802, in alternative implementations, database 806 can be external to the computer 802.

The computer 802 also includes a memory 807 that can hold data for the computer 802 or a combination of components connected to the network 830 (whether illustrated or not). Memory 807 can store any data consistent with the present disclosure. In some implementations, memory 807 can be a combination of two or more different types of memory (for example, a combination of semiconductor and magnetic storage) according to particular needs, desires, or particular implementations of the computer 802 and the described functionality. Although illustrated as a single memory 807 in FIG. 8, two or more memories 807 (of the same, different, or combination of types) can be used according to particular needs, desires, or particular implementations of the computer 802 and the described functionality. While memory 807 is illustrated as an internal component of the computer 802, in alternative implementations, memory 807 can be external to the computer 802.

The application 808 can be an algorithmic software engine providing functionality according to particular needs, desires, or particular implementations of the computer 802 and the described functionality. For example, application 808 can serve as one or more components, modules, or applications. Further, although illustrated as a single application 808, the application 808 can be implemented as multiple applications 808 on the computer 802. In addition, although illustrated as internal to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion and management circuits, including recharging, standby, and power management functionalities. In some implementations, the power supply 814 can include a power plug to allow the computer 802 to be plugged into a wall socket or a power source to, for example, power the computer 802 or recharge a rechargeable battery.

There can be any number of computers 802 associated with, or external to, a computer system containing computer 802, with each computer 802 communicating over network 830. Further, the terms "client," "user," and other appropriate terminology can be used interchangeably, as appropriate, without departing from the scope of the present disclosure. Moreover, the present disclosure contemplates that many users can use one computer 802 and one user can use multiple computers 802.

Described implementations of the subject matter can include one or more features, alone or in combination.

For example, in a first implementation, a computer-implemented method includes the following. Units of smart polymers with hydrogen sulfide (H2S) sensitivity are inserted by a monitoring system into drilling fluid pumped into a well during a drilling operation. The smart polymers are configured to be triggered by increasing H2S concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of H2S levels at a drill bit of the drilling operation is determined by the monitoring system using the continuous images and the observed characteristics and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the H2S levels.

The foregoing and other described implementations can each, optionally, include one or more of the following features:

A first feature, combinable with any of the following features, where the units of smart polymers have a pill shape.

A second feature, combinable with any of the previous or following features, where the method further includes pumping the units of smart polymers into the drilling fluid at different intervals or every one stand.

A third feature, combinable with any of the previous or following features, where the units of smart polymers are configured to change properties as a function of changing H2S concentrations exposed to the units of smart polymers by downhole conditions.

A fourth feature, combinable with any of the previous or following features, where capturing the continuous images includes capturing, in the units of smart polymers, evidence of changing H2S levels caused by H2S exposure experienced by the units of smart polymers.

A fifth feature, combinable with any of the previous or following features, where determining the H2S levels includes correlating an arrival timestamp identifying a time of arrival of each unit of smart polymer at the sensing location with a respective hole depth by utilizing a rig sensor for mud flow rate and based on an annular area of the well.

A sixth feature, combinable with any of the previous or following features, where the sensing location is selected from the group consisting of a shale shaker, a centrifuge, a de-sander, and a de-silter.

In a second implementation, a non-transitory, computer-readable medium stores one or more instructions executable by a computer system to perform operations including the following. Units of smart polymers with hydrogen sulfide (H2S) sensitivity are inserted by a monitoring system into drilling fluid pumped into a well during a drilling operation. The smart polymers are configured to be triggered by increasing H2S concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of H2S levels at a drill bit of the drilling operation is determined by the monitoring system using the continuous images and the observed characteristics and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the H2S levels.

The foregoing and other described implementations can each, optionally, include one or more of the following features:

A first feature, combinable with any of the following features, where the units of smart polymers have a pill shape.

A second feature, combinable with any of the previous or following features, where the operations further include pumping the units of smart polymers into the drilling fluid at different intervals or every one stand.

A third feature, combinable with any of the previous or following features, where the units of smart polymers are configured to change properties as a function of changing H2S concentrations exposed to the units of smart polymers by downhole conditions.

A fourth feature, combinable with any of the previous or following features, where capturing the continuous images includes capturing, in the units of smart polymers, evidence of changing H2S levels caused by H2S exposure experienced by the units of smart polymers.

A fifth feature, combinable with any of the previous or following features, where determining the H2S levels includes correlating an arrival timestamp identifying a time of arrival of each unit of smart polymer at the sensing location with a respective hole depth by utilizing a rig sensor for mud flow rate and based on an annular area of the well.

A sixth feature, combinable with any of the previous or following features, where the sensing location is selected from the group consisting of a shale shaker, a centrifuge, a de-sander, and a de-silter.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Units of smart polymers with hydrogen sulfide (H2S) sensitivity are inserted by a monitoring system into drilling fluid pumped into a well during a drilling operation. The smart polymers are configured to be triggered by increasing H2S concentrations. An insertion timestamp associated with each unit is stored by the monitoring system. Each insertion timestamp indicates a time that each unit was inserted into the drilling fluid. Continuous images and observed characteristics of returning mud exiting through an annulus of the well and containing the units of smart polymer are captured by a camera positioned at a sensing location and linked to the monitoring system. An estimate of H2S levels at a drill bit of the drilling operation is determined by the monitoring system using the continuous images and the observed characteristics and the insertion timestamps associated with each unit of smart polymer. Determining the estimate is based at least in part on executing image processing algorithms, machine-learning models, and deep-learning models. Changes to be made to drilling parameters for the drilling operation are suggested by the monitoring system based at least in part on the estimate of the H2S levels.

The foregoing and other described implementations can each, optionally, include one or more of the following features:

A first feature, combinable with any of the following features, where the units of smart polymers have a pill shape.

A second feature, combinable with any of the previous or following features, where the operations further include pumping the units of smart polymers into the drilling fluid at different intervals or every one stand.

A third feature, combinable with any of the previous or following features, where the units of smart polymers are configured to change properties as a function of changing H2S concentrations exposed to the units of smart polymers by downhole conditions.

A fourth feature, combinable with any of the previous or following features, where capturing the continuous images includes capturing, in the units of smart polymers, evidence of changing H2S levels caused by H2S exposure experienced by the units of smart polymers.

A fifth feature, combinable with any of the previous or following features, where determining the H2S levels includes correlating an arrival timestamp identifying a time of arrival of each unit of smart polymer at the sensing location with a respective hole depth by utilizing a rig sensor for mud flow rate and based on an annular area of the well.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or TO S.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback, including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at the application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:
1. A computer-implemented method, comprising:
 inserting, by a monitoring system, units of smart polymers with hydrogen sulfide (H2S) sensitivity into drilling fluid pumped into a well during a drilling operation, the smart polymers configured to be triggered by increasing hydrogen sulfide (H2S) concentrations;
 storing, by the monitoring system, an insertion timestamp associated with each unit, each insertion timestamp indicating a time that each unit was inserted into the drilling fluid;

capturing, by a camera positioned at a sensing location and linked to the monitoring system, continuous images and observed characteristics of returning mud exiting through an annulus of the well and containing the units of smart polymer;

determining, by the monitoring system and using the continuous images and the observed characteristics and the insertion timestamps associated with each unit of smart polymer, an estimate of H2S levels at a drill bit of the drilling operation, wherein determining the estimate is based at least in part on executing image processing algorithms, machine-learning models, and deep-learning models; and suggesting, by the monitoring system and based at least in part on the estimate of the H2S levels, changes to be made to drilling parameters for the drilling operation.

2. The computer-implemented method of claim 1, wherein the units of smart polymers have a pill shape.

3. The computer-implemented method of claim 1, further comprising:
pumping the units of smart polymers into the drilling fluid at different intervals or every one stand.

4. The computer-implemented method of claim 1, wherein the units of smart polymers are configured to change properties as a function of changing H2S concentrations exposed to the units of smart polymers by downhole conditions.

5. The computer-implemented method of claim 1, wherein capturing the continuous images includes capturing, in the units of smart polymers, evidence of changing H2S levels caused by H2S exposure experienced by the units of smart polymers.

6. The computer-implemented method of claim 1, wherein determining the H2S levels includes correlating an arrival timestamp identifying a time of arrival of each unit of smart polymer at the sensing location with a respective hole depth by utilizing a rig sensor for mud flow rate and based on an annular area of the well.

7. The computer-implemented method of claim 1, wherein the sensing location is selected from the group consisting of a shale shaker, a centrifuge, a de-sander, and a de-silter.

8. A non-transitory, computer-readable medium storing one or more instructions executable by a computer system to perform operations comprising:
inserting, by a monitoring system, units of smart polymers with hydrogen sulfide (H2S) sensitivity into drilling fluid pumped into a well during a drilling operation, the smart polymers configured to be triggered by increasing hydrogen sulfide (H2S) concentrations;

storing, by the monitoring system, an insertion timestamp associated with each unit, each insertion timestamp indicating a time that each unit was inserted into the drilling fluid;

capturing, by a camera positioned at a sensing location and linked to the monitoring system, continuous images and observed characteristics of returning mud exiting through an annulus of the well and containing the units of smart polymer;

determining, by the monitoring system and using the continuous images and the observed characteristics and the insertion timestamps associated with each unit of smart polymer, an estimate of H2S levels at a drill bit of the drilling operation, wherein determining the estimate is based at least in part on executing image processing algorithms, machine-learning models, and deep-learning models; and suggesting, by the monitoring system and based at least in part on the estimate of the H2S levels, changes to be made to drilling parameters for the drilling operation.

9. The non-transitory, computer-readable medium of claim 8, wherein the units of smart polymers have a pill shape.

10. The non-transitory, computer-readable medium of claim 8, the operations further comprising:
pumping the units of smart polymers into the drilling fluid at different intervals or every one stand.

11. The non-transitory, computer-readable medium of claim 8, wherein the units of smart polymers are configured to change properties as a function of changing H2S concentrations exposed to the units of smart polymers by downhole conditions.

12. The non-transitory, computer-readable medium of claim 8, wherein capturing the continuous images includes capturing, in the units of smart polymers, evidence of changing H2S levels caused by H2S exposure experienced by the units of smart polymers.

13. The non-transitory, computer-readable medium of claim 8, wherein determining the H2S levels includes correlating an arrival timestamp identifying a time of arrival of each unit of smart polymer at the sensing location with a respective hole depth by utilizing a rig sensor for mud flow rate and based on an annular area of the well.

14. The non-transitory, computer-readable medium of claim 8, wherein the sensing location is selected from the group consisting of a shale shaker, a centrifuge, a de-sander, and a de-silter.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
inserting, by a monitoring system, units of smart polymers with hydrogen sulfide (H2S) sensitivity into drilling fluid pumped into a well during a drilling operation, the smart polymers configured to be triggered by increasing hydrogen sulfide (H2S) concentrations;

storing, by the monitoring system, an insertion timestamp associated with each unit, each insertion timestamp indicating a time that each unit was inserted into the drilling fluid;

capturing, by a camera positioned at a sensing location and linked to the monitoring system, continuous images and observed characteristics of returning mud exiting through an annulus of the well and containing the units of smart polymer;

determining, by the monitoring system and using the continuous images and the observed characteristics and the insertion timestamps associated with each unit of smart polymer, an estimate of H2S levels at a drill bit of the drilling operation, wherein determining the estimate is based at least in part on executing image processing algorithms, machine-learning models, and deep-learning models; and suggesting, by the monitoring system and based at least in part on the estimate of the H2S levels, changes to be made to drilling parameters for the drilling operation.

16. The computer-implemented system of claim 15, wherein the units of smart polymers have a pill shape.

17. The computer-implemented system of claim 15, the operations further comprising:
   pumping the units of smart polymers into the drilling fluid at different intervals or every one stand.

18. The computer-implemented system of claim 15, wherein the units of smart polymers are configured to change properties as a function of changing H2S concentrations exposed to the units of smart polymers by downhole conditions.

19. The computer-implemented system of claim 15, wherein capturing the continuous images includes capturing, in the units of smart polymers, evidence of changing H2S levels caused by H2S exposure experienced by the units of smart polymers.

20. The computer-implemented system of claim 15, wherein determining the H2S levels includes correlating an arrival timestamp identifying a time of arrival of each unit of smart polymer at the sensing location with a respective hole depth by utilizing a rig sensor for mud flow rate and based on an annular area of the well.

* * * * *